(12) United States Patent
Rong et al.

(10) Patent No.: US 8,506,887 B2
(45) Date of Patent: Aug. 13, 2013

(54) POROUS MEMBRANE WAVEGUIDE SENSORS AND SENSING SYSTEMS THEREFROM FOR DETECTING BIOLOGICAL OR CHEMICAL TARGETS

(75) Inventors: Guoguang Rong, Shanghai (CN); Raymond L. Mernaugh, Franklin, TN (US); Sharon M. Weiss, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 80 days.

(21) Appl. No.: 12/581,082

(22) Filed: Oct. 16, 2009

(65) Prior Publication Data

US 2010/0098592 A1  Apr. 22, 2010

Related U.S. Application Data

(60) Provisional application No. 61/196,502, filed on Oct. 17, 2008.

(51) Int. Cl.
*G01N 21/00* (2006.01)
*G01N 21/75* (2006.01)
*G02B 6/00* (2006.01)
*C12M 1/34* (2006.01)

(52) U.S. Cl.
USPC ..... 422/82.11; 422/400; 422/401; 422/82.05; 436/164; 436/165; 385/12; 385/15; 385/36; 385/37; 385/141; 356/446; 356/447; 356/448; 356/73.1; 435/283.1; 435/287.2; 435/288.7

(58) Field of Classification Search
None
See application file for complete search history.

(56) References Cited

U.S. PATENT DOCUMENTS

| | | | | |
|---|---|---|---|---|
| 5,991,488 | A * | 11/1999 | Salamon et al. | 385/129 |
| 6,248,539 | B1 | 6/2001 | Ghadiri et al. | |
| 7,075,657 | B2 * | 7/2006 | Sato | 356/455 |
| 7,226,733 | B2 | 6/2007 | Chan et al. | |
| 2006/0234391 | A1 * | 10/2006 | Weiss et al. | 436/518 |

OTHER PUBLICATIONS

Applied Physics Letter 90, 011102 (2007) "Nanoporous Leaky Waveguide Based on Chemical and Biological Sensors With Broadband Spectroscopy"; Zhi-Mei Qi, Itaru Honma, and Haoshen Zhou. J. Phys. Chem. B 2004, 108, pp. 10812-10818; "Highly Sensitive Detection of Processes Occurring Inside Nanoporous Anodic Alumina Templates: A Waveguide Optical Study"; King Hang Aaron Lau; Le-Shon Tan; Kaoru Tamada; Melissa S. Sander, Wolfgang Knoll.

(Continued)

*Primary Examiner* — Neil N Turk
(74) *Attorney, Agent, or Firm* — Novak Druce Connolly Bove + Quigg LLP; Eduardo J. Quinones

(57) ABSTRACT

A sensor for sensing at least one biological target or chemical target is provided. The sensor includes a membrane includes a membrane material that supports generation and propagation of at least one waveguide mode, where the membrane material includes a plurality of voids having an average size<2 microns. The sensor also includes at least one receptor having structure for binding to the target within the plurality of voids, and an optical coupler for coupling light to the membrane sufficient to generate the waveguide mode in the membrane from photons incident on the optical coupler.

13 Claims, 9 Drawing Sheets

(56) References Cited

OTHER PUBLICATIONS vol. 15, No. 5/Optics Express 2597; High Sensitiving Sensors Made of Perforated Waveguides; Koichi Awazu; Carsten Rockstuhl; Makoto Fujimaki; Nobuko Fukuda; Junji Tominaga; Tetsuro Komatsubara; Takahiro Ikeda; Yoshimichi Ohki.

Ouyang, Huimin et al., "Macroporous Silicon Microcavities for Macromolecule Detection," Advanced Functional Materials 2005, 15, pp. 1851-1859.

Saarinen, Jarkko J. et al., "Optical sensor based on resonant porous silicon structures," Optics Express, May 16, 2005, vol. 13, No. 10, pp. 3754-3764.

R. Herino et al., "Porosity and Pore Size Distributions of Porous Silicon Layers," J. Electrocem. Soc. Solid-State Science and Technology vol. 134, No. 8, Aug. 1987, pp. 1994-2000.

L. Pavesi, "Porous silicon dielectric multilayers and microcavities," Rivista Del Nuovo Cimento, vol. 20, No. 10, Sep. 16, 1997, pp. 1-76.

* cited by examiner

100

200

300

400

500

600

700

800

1000

“POROUS MEMBRANE WAVEGUIDE SENSORS AND SENSING SYSTEMS THEREFROM FOR DETECTING BIOLOGICAL OR CHEMICAL TARGETS”

CROSS REFERENCE TO RELATED APPLICATIONS

This application claims the benefit of Provisional Application Ser. No. 61/196,502 entitled "POROUS MEMBRANE WAVEGUIDE SENSORS AND SENSING SYSTEMS THEREFROM FOR DETECTING BIOLOGICAL OR CHEMICAL TARGETS", filed Oct. 17, 2008, which is herein incorporated by reference in its entirety.

FEDERAL RIGHTS

The U.S. Government has certain rights to embodiments of the present invention based on National Science Foundation Grant ECCS-0746296 and Army Research Office Grant W911NF-08-1-0200.

FIELD OF THE INVENTION

The invention pertains to membrane-based sensors for detecting chemical or biological targets.

BACKGROUND

The detection of biomolecules and certain chemicals is important for a wide variety of applications. Applications for biomolecule sensing include medical diagnostics, food safety, and anti-bioterrorism. Conventional biosensors often include fluorescent reporter labels to generate a detection signal.

Label-free biosensors and chemical sensors can directly measure unmodified samples without the need for reporter molecules. Such label-free sensors generally operate based on a change in refractive index due to affinity binding events of biomolecules or chemicals. For example, biomolecules immobilized on the surface of surface plasmon resonance (SPR), fiber optic, and planar waveguide sensors interact with the evanescent field of either the surface plasmon or waveguide mode and cause a refractive index change near the surface of these sensors. However, these evanescent wave sensors are limited in sensitivity, especially for small molecule (e.g. 200-1,000 Daltons) detection, since the surface area is small and the interaction between biomolecules or chemicals and the electromagnetic field is generally fairly weak.

SUMMARY

This Summary is provided to comply with 37 C.F.R. §1.73, presenting a summary of the invention to briefly indicate the nature and substance of the invention. It is submitted with the understanding that it will not be used to interpret or limit the scope or meaning of the claims. Embodiments of the present invention describe porous membrane waveguide sensors and sensing systems for detecting biological or chemical targets.

In a first embodiment of the invention, a sensor for sensing at least one biological target or chemical target is provided. The sensor includes a membrane comprising a membrane material that supports generation and propagation of at least one waveguide mode, the membrane material comprising a plurality of voids having an average size<2 microns. The sensor also includes at least one receptor having structure for binding to the target immobilized within the plurality of voids, and an optical coupler for coupling light to the membrane sufficient to generate the waveguide mode in the membrane from photons incident on the optical coupler.

In a second embodiment of the invention, a sensor chip is provided. The sensor chip includes an optically transparent support material and a membrane comprising a membrane material on the support that supports generation and propagation of at least waveguide mode. The membrane material includes a plurality of voids having an average size<2 microns. The sensor chip also includes at least one receptor having structure for binding to the target immobilized within the plurality of voids, and a cladding layer interposed between the optically transparent support material and the membrane.

In a third embodiment of the invention, a sensing system is provided. The system includes a sensor for sensing at least one biological target or chemical target. The sensor includes a substrate support layer and a membrane comprising a membrane material that supports generation and propagation of at least one waveguide mode on the support layer. The membrane material includes a plurality of voids having an average size<2 microns. The sensor also includes at least one receptor having structure for binding to the target immobilized within the plurality of voids. The system also includes an optical block operable for coupling light to the membrane sufficiently to generate the waveguide mode in the membrane from photons propagating in the optical block. The system also includes a light source for providing the photons, and a light detector for detecting the photons that are reflected by the optical block.

DETAILED DESCRIPTION

Figure 1:
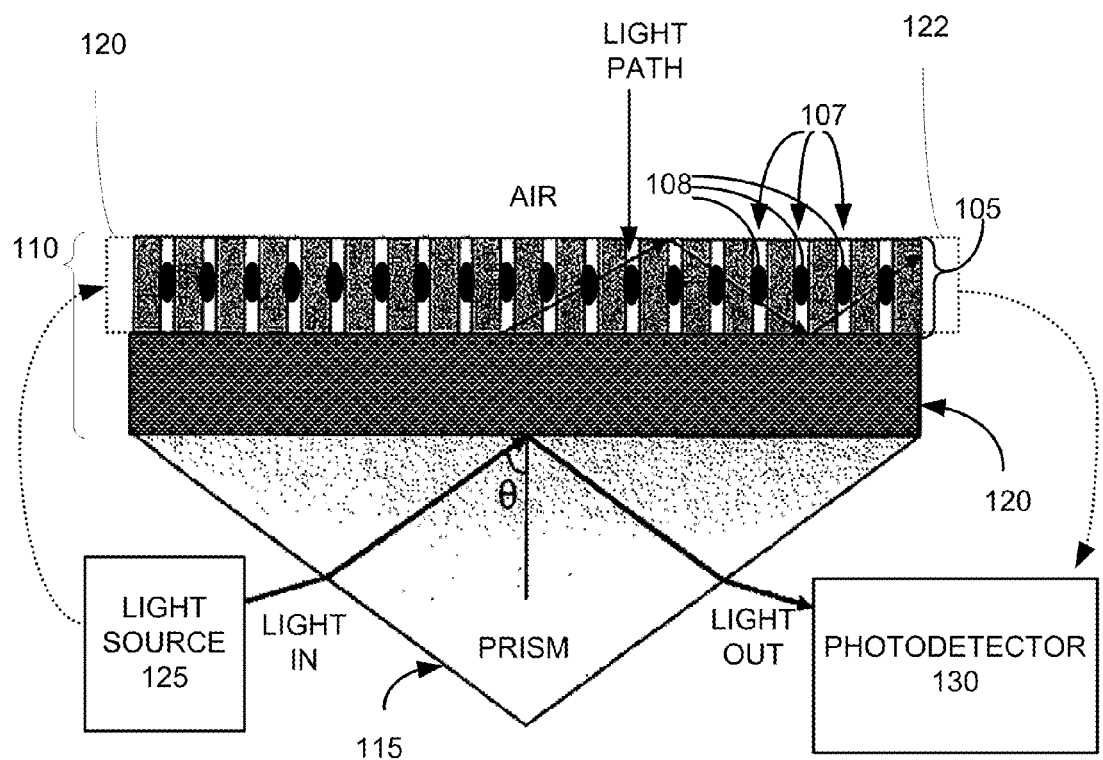
FIG. 1 is a depiction of a first exemplary sensor system including a porous membrane waveguide sensor according to an embodiment of the invention for sensing at least one biological target or chemical target.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention describe porous membrane waveguide sensors for sensing at least one biological target or chemical target. The porous membrane waveguide sensors comprise a membrane material that supports generation and propagation of at least one waveguide mode, wherein the membrane includes a plurality of voids having receptor molecules therein. As known in the art, support of waveguide modes is a characteristic of an optical waveguide that can comprise a dielectric or a semiconductor material. As defined herein, the term "membrane" as used in "porous membrane" refers to a layer having a thickness≦10 microns. Moreover, the term "porous" as used herein in "porous membrane" refers to layer having a plurality of voids over at least a portion of the area and the thickness of the layer, wherein the effective refractive index of portion including the voids is≦90% of the refractive index of the bulk (non-void comprising) membrane material.

As defined herein, the term "waveguide mode", refers to both guided and leaky modes in an optical waveguide. A guided, bound, or trapped mode in an optical waveguide is a mode that (a) has an electric field that decays monotonically in the transverse direction everywhere external to the core and (b) does not lose power to radiation. A leaky mode or tunneling mode in an optical waveguide is a mode having an electric field that decays monotonically for a finite distance in the transverse direction but becomes oscillatory everywhere beyond that finite distance. Such a mode gradually "leaks" out of the waveguide as it travels down it, producing attenuation.

There is a wide variety of different optical waveguiding materials that support at least one waveguide mode, with the only requirements being that the material is surrounded by one or more lower refractive index "cladding" materials and that the waveguide material does not completely absorb or absorb too much light at the wavelength to be excited. As used herein, the term "light", is not limited to visible light, and generally also includes the ultraviolet, infrared and a portion of the microwave range. A few non-limiting examples of waveguide materials that can be used with embodiments of the invention as the membrane material include certain polymers, glass, certain nonlinear materials such as lithium niobate, and semiconductor materials. Semiconductor materials can include as column IV semiconductors, III-V semiconductors, IV-VI semiconductor materials, or any variants or mixtures thereof. In some embodiments, metal comprising materials can also be used, such as optical metal oxide materials.

In the various embodiments of the invention, the porous membrane material can be formed in a variety of ways. For example, in some embodiments of the invention, the porous membrane material can be formed by applying an etching agent to a non-porous material in order to form voids in the non-porous material. In some embodiments of the invention, the voids in porous membrane material can be formed during formation of the porous membrane material. For example, a material or a process for forming a material can be utilized that is susceptible to the formation of voids. Alternatively materials or processes that result in structures having voids can also be used, such as carbon nanotubes.

In order to support guided and leaky mode propagation, the voids in the membrane material should generally have an average size that is significantly less than the wavelength of light propagating therein. In the exemplary case of 1550 nm (1.55 micron) light, the void size should generally be<1 micron, such as<0.5 micron. However, for most waveguide materials the membrane material can generally support light propagation at much longer wavelengths, which allows for larger void sizes. However, obtaining compact, cost-effective light sources for longer wavelengths (e.g. 10 microns) may pose a challenge.

The thickness of the porous membrane generally determines the number of guided modes supported, with more modes being supported for higher thicknesses. In most embodiments of the invention, the membrane thickness is between 100 nm and several microns thick, such as 5 microns, for guided modes. For leaky modes, the membrane thickness can be thinner. The minimum membrane thickness generally depends on the refractive index of the cladding and the membrane material and the wavelength of light used, with the minimum thickness for an exemplary porous silicon waveguide and polymer cladding being on the order of a few hundred nanometers. There are characteristic equations that can be solved to determine the minimum membrane thickness based on these parameters. Generally, as the refractive index contrast between the porous membrane waveguiding layer and cladding layer decreases, the minimum membrane thickness increases. For example, in traditional fiber technology where the refractive index contrast can be on the order one percent, the minimum membrane thickness generally being on the order of a few to several microns.

An increase in the number of waveguide modes contributes to modal dispersion losses and the various higher order waveguide modes are not quite as well confined as the zero-order mode. Another significant drawback of a very thick porous membrane is generally the diffusion time required for receptor molecules to diffuse into the depth of the porous membrane.

At least one receptor having structure for binding to the target is immobilized within the plurality of voids. The receptors can comprise receptors such as a chemical receptor, a bioreceptor, a polymer, a biopolymer, a molecular imprint polymer, a biomimetic, an antibody, an enzyme, a cell receptor, a molecular print assay, or a nucleic acid. The sensor also includes one or more optical blocks operable for coupling light to the porous membrane sufficient to generate at least one waveguide mode in the membrane material from photons incident on the optical block. The optical coupler can comprise a prism or a grating coupler, as illustrated below in FIGS. 1-4.

In typical operation, when the target is present and exposed to the receptors that are in the voids, the target becomes bound to the receptors, thus increasing the refractive index of the porous membrane. The change in the refractive index of the porous membrane changes the waveguide mode dispersion characteristics including a change in the waveguide resonance angle which corresponds to the angle at which the light in the optical coupler couples into the porous membrane, and a change in the intensity of light propagating in the porous membrane waveguide. Thus, if the target molecules bind to the receptors, then their presence can be detected by a change in resonance angle or a change in intensity of light exiting the porous membrane waveguide. Moreover, the change in waveguide resonance angle and change in intensity has been found to be related to the concentration of the target, such as being nearly linear with the target concentration. If a broadband source or tunable light source is used, a change in resonance wavelength could also be monitored to determine when targets are bound to receptors.

FIG. 1 is a depiction of an exemplary sensor system 100 including a porous membrane waveguide sensor 110 according to am embodiment of the invention for sensing at least one biological target or chemical target. Sensor 110 includes a porous membrane 105 comprising a membrane material that supports generation and propagation of at least one waveguide mode. The porous membrane 105 includes a plurality of voids 107 having an average size<5 microns, wherein at least one receptor 108 which has a structure for binding to the target is immobilized within the voids 107. In some embodiments of the invention, the voids can comprise cylindrical voids. In such embodiments, the voids can have a diameter that is from 5 to 100 nm and the receptors line the void surface. The receptors will generally be immobilized onto the surfaces of the voids.

Sensor 110 includes an optical coupler shown as a prism 115 for coupling light (shown as light in) to the porous membrane 105 from a light source 125 (e.g. laser) sufficient to generate at least one waveguide mode for light propagating through membrane 105 (shown as light path) from the light transmitted by the prism 115. Absorption losses are minimized by sensor 110 because light is coupled to the porous membrane waveguide 105 through a low loss path comprising prism 115 and cladding 120, in contrast to arrangements that require coupling of light through high loss paths such as through thick support layers such as 500 micron thick silicon substrates. In arrangements using silicon substrates, lower doped silicon substrates can be used to reduce losses in the visible spectrum. Moreover, porous membrane 105 is the only porous layer in sensor 110. Sensor 110 (and sensor 210 described below relative to FIG. 2) have the advantage over sensors that have two (or more) porous layers since all target molecules exposed to the sensor 110 remain in the porous membrane waveguiding layer 105 where they are most sensitively detected. This results in enhanced sensitivity since fewer target molecules need to be exposed to the sensor 110 in order to produce a positive response.

There is generally no need for the light source to provide polarized light. If unpolarized light is used, two waveguide modes, one for transverse electric (TE)-polarization where the electric field vector is perpendicular to the plane of incidence, and one for transverse magnetic (TM)-polarization where the magnetic field vector is perpendicular to the plane of incidence, will be observed at resonance. However, generally, no additional information is gained by the presence of the two modes so, for simplicity, as described herein, only one of the two modes, arbitrarily chosen as the TE mode, is usually excited. Sensor 110 also includes a cladding layer 120 between the porous membrane 105 and the prism 115 for improving confinement of the waveguide mode(s) in the porous membrane 105. Air (or other ambient) or a liquid buffer material on the other side of porous membrane 105 also provides cladding for porous membrane 105.

In one embodiment of the invention the cladding layer 120 comprises a polymer film, such as a Formvar polymer film. Such a polymer serves to provide robust attachment of the porous membrane 105 to the prism 115. However, the confinement of the waveguide mode(s) in the porous membrane 105 would generally be better if a lower index material were used for cladding layer instead of a polymer cladding layer, such as air in the case of an air gap.

Light propagating in prism 115 is shown reflecting at the interface between the prism 115 and the cladding layer 120. Reflected light shown as "light out" emerges from the prism 115 and is detected by a suitable photodetector 130, such as a CCD-based photodetector.

As noted above, system 100 can detect the presence of biological and chemical targets with high sensitivity based on the induced refractive index change of the porous membrane 105 when the target molecule is bound to the receptors 108 which can be detected as described above in various ways, such as a change in the waveguide resonance angle, waveguide resonance wavelength, or intensity of light propagating in the porous membrane. In contrast, conventional technologies for chemical and biological sensing typically rely on relatively weak interaction of evanescent fields with molecules on flat surfaces. The limited surface area of these conventional sensors, combined with their reliance on evanescent fields, is especially troublesome for the detection of small molecules. Conventional sensors (e.g. SPR) are also limited in their ability to detect larger particles (e.g. viruses) due to a loss in evanescence at a distance (e.g. the distal end of a virus) from the sensor surface. Sensors according to embodiments of the present invention overcome this disadvantage provided the voids are large enough to accommodate these larger particles.

Sensors according to embodiments of the invention such as sensor 110 have a very large surface area provided by the porous membrane 105. Moreover, such sensors provide excellent field confinement in the porous membrane 105 where receptors 108 are immobilized, and as described below relative to FIG. 2 can be configured to be highly compatible with current commercial sensor instrumentation.

Figure 2:
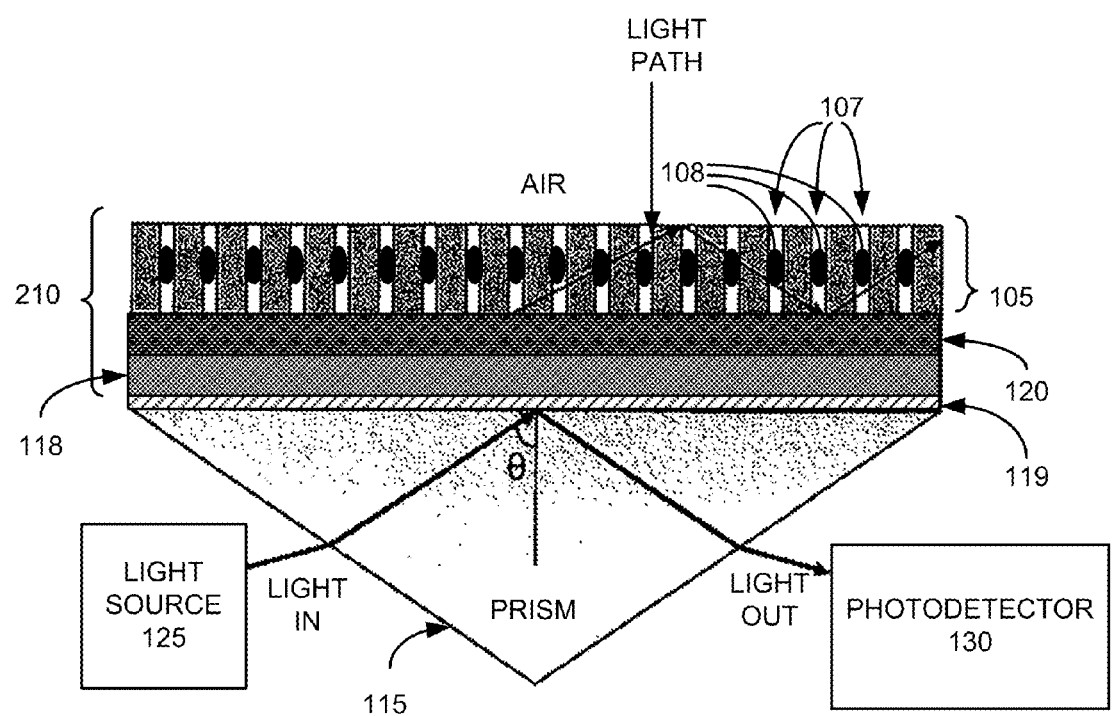
FIG. 2 is a depiction of a second exemplary sensor system including a porous membrane waveguide sensor according to an embodiment of the invention for sensing at least one biological target or chemical target.

One embodiment for sensors according to embodiments of the invention involves the fabrication of sensor chips that can be directly inserted into commercial surface plasmon resonance (SPR) sensor instruments. SPR sensor instruments currently dominate the market for biosensing applications. FIG. 2 shows a depiction of an exemplary porous membrane waveguide sensor system 200 including a porous waveguide sensor 210 according to an embodiment of the invention in a sensor "chip" configuration. A sensor 210 in the sensor chip configuration shown in FIG. 2 is adapted for being an independent, potentially disposable, component that can be purchased separately from, and at a lower cost than, the more complex and expensive commercially available or otherwise known measurement instrument. Moreover, sensor chip 210 will generally be cheaper to fabricate and enable lower detection limits for small molecules that presently cannot be detected with high accuracy in most commercial sensor devices, such as those based on SPR.

Sensor chip 210 includes porous membrane 105, a support layer 118 and cladding layer 120. The sensor chip 210 is generally self supported and can be an independent, potentially disposable component. The support layer 118 makes the sensor chip 210 robust enough to be transported and manipulated by users, such as for direct insertion into existing measurement instrumentation (e.g. SPR-based instrumentation). The existing instrumentation (e.g. SPR) generally provides the prism 115 and index matching layer 119, which is generally a liquid.

In order to couple light into the porous membrane waveguide 105 in system 200, the refractive index of the prism 115, index matching material 119, and the support layer 118 should all be about the same. The index matching layer 119 and support layer 118 are effectively an extension of the prism interface so that total internal reflection occurs at the support layer/cladding interface. Total internal reflection is generally needed to generate the evanescent field that allows light to be coupled into the porous membrane waveguide 105. Without the index matching between the prism 115, index matching material 119, and support layer 118, the evanescent wave might be generated at the prism interface and die out before reaching the cladding layer 120. Support layer 118 can be embodied as a glass slide or optically transparent plastic or resin, or other material to generally result in support layer 118 not having a lower refractive index than the prism 115.

As with sensor 110 described relative to FIG. 1, absorption losses are minimized by sensor 210 because light is coupled to the porous membrane waveguide 105 through a low loss path comprising prism 115, index matching layer 119, support layer 118 and cladding 120, in contrast to arrangements that require coupling of light through high loss paths such as through thick support layers such as thick (e.g. 500 micron) silicon substrates.

Figure 3:
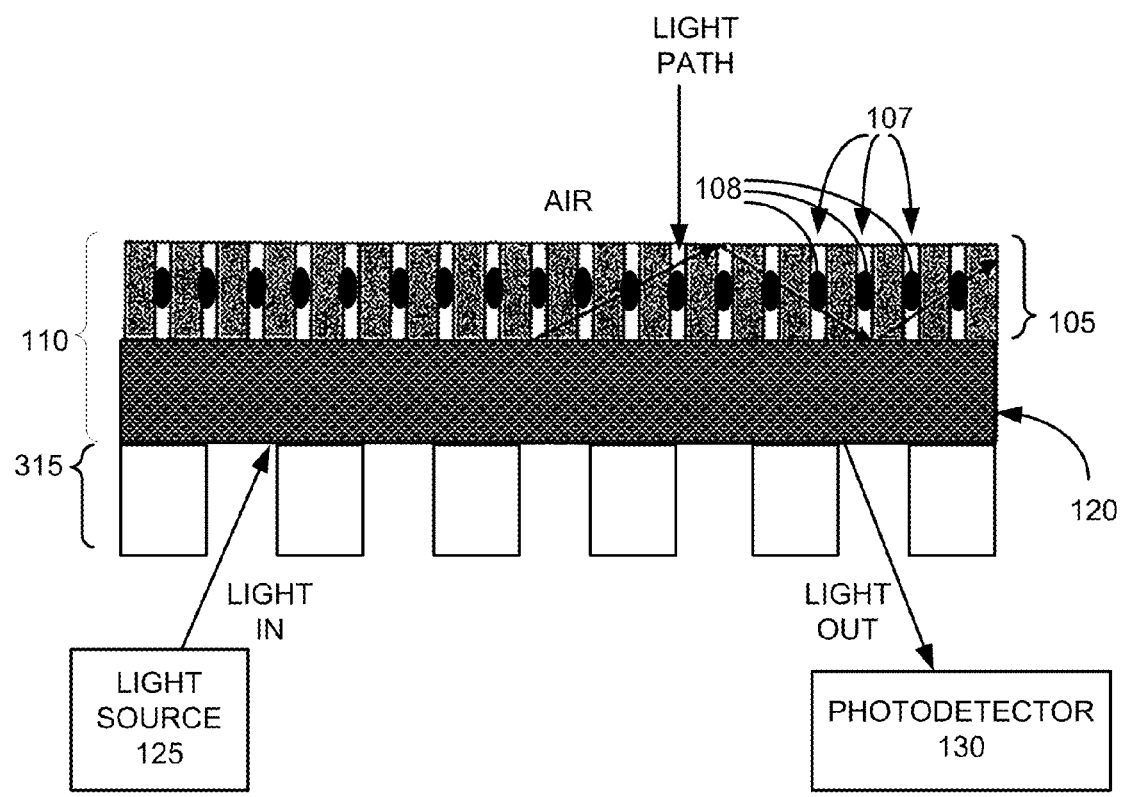
FIG. 3 is a depiction of a third exemplary sensor system including a porous membrane waveguide sensor according to an embodiment of the invention for sensing at least one biological target or chemical target.
Figure 4:
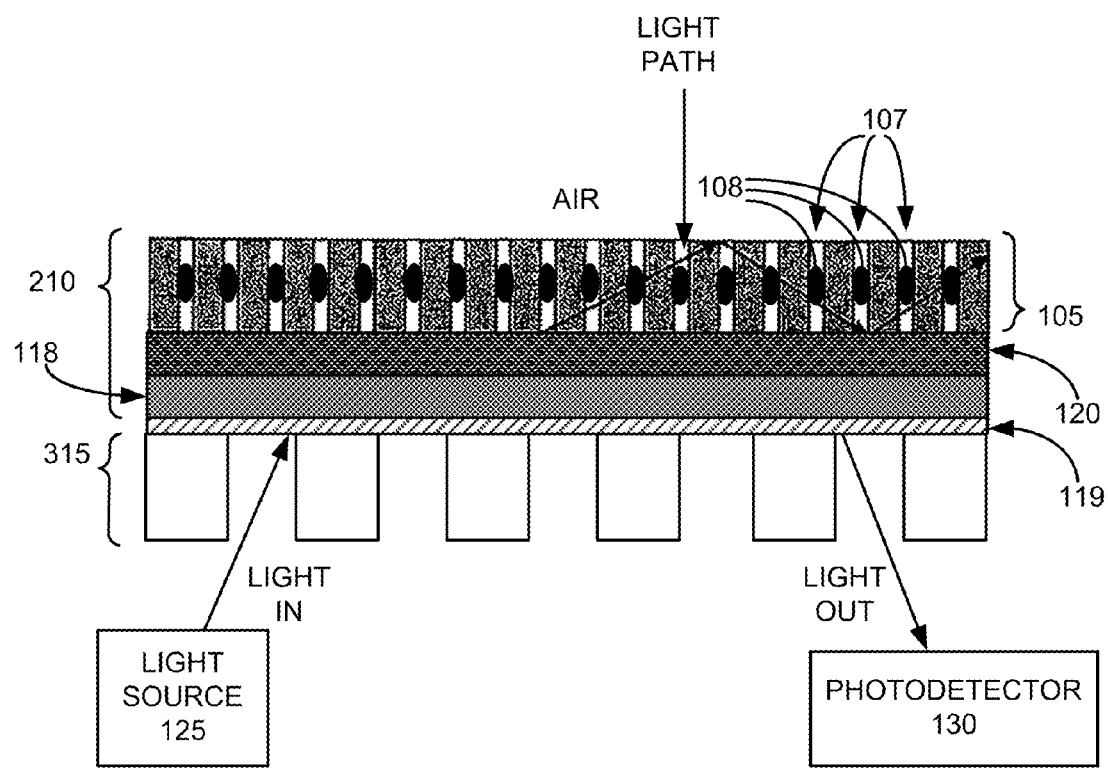
FIG. 4 is a depiction of a fourth exemplary sensor system including a porous membrane waveguide sensor according to an embodiment of the invention for sensing at least one biological target or chemical target.

As described above, sensors according to embodiments of the invention can also utilize grating couplers instead of prisms as the optical coupler. This is illustrated in FIGS. 3 and 4. FIG. 3 is a depiction of an exemplary sensor system 300 including a porous membrane waveguide sensor 110 and a grating coupler 315 according to am embodiment of the invention for sensing at least one biological target or chemical target. FIG. 4 shows a depiction of an exemplary porous membrane waveguide sensor system 400 including a porous waveguide sensor 210 and a grating coupler 315 according to an embodiment of the invention in a sensor "chip" configuration.

The exemplary systems shown in FIGS. 3 and 4 are substantially similar to those described above with respect to FIGS. 1 and 2, respectively. Accordingly, the description above for FIGS. 1 and 2 is sufficient for describing the exemplary systems shown in FIGS. 3 and 4, respectively. As described above, in FIGS. 3 and 4, the prism has been replaced with grating coupler 315. In the embodiments shown in FIGS. 3 and 4, the grating coupler 315 need not be optically transparent as in the case of the optical coupler being a prism described above relative to FIGS. 1 and 2. In the various embodiments of the invention, the configuration of the grating coupler (i.e., its dimensions, including grating spacing) can be selected to provide a coupling angle that generates one or more waveguide modes in either of sensors 110 and 210.

The use of grating couplers in the various embodiments of the invention is not limited to the configurations shown in FIGS. 3 and 4. In some embodiments of the invention, the grating coupler and the membrane can be fabricated together. That is, the sensor can be fabricated from a single portion of membrane material in which the plurality of voids are formed on one side and gratings on a second side.

Optical couplers besides prisms or gratings may also generally be used with embodiments of the invention. For example, a tapered fiber can be used in place of a prism or grating. Also, as shown by the dashed path in FIG. 1, light can instead be launched in the waveguide from one end face, instead of the top surface, via butt-coupling with a fiber, end-fire couplings 120, 125 from free-space light focused by a lens, or coupling from a tapered waveguide. All of these alternatives to prism or grating-based couplers generally require a measurement of the intensity of light at the opposite end of the waveguide in order to determine whether target molecules are bound inside the waveguide.

Sensors according to embodiments of the invention can be embodied in a wide variety of different embodiments. For example, it is possible to design such sensors without any solid cladding layers. For example, a flow-through sensor chip can be configured with a fixed thickness air gap between the prism or other optical coupler and the porous membrane. Moreover, although sensors are generally described herein for detecting a specific biological or chemical target, sensors according to embodiments of the invention can include porous membranes comprising a plurality of regions each having different receptors within the voids provided in the regions, wherein the different receptors are each adapted to bind with different targets. For example, a porous membrane can include a plurality of regions which each sense a different target, including control regions. For example, a region of the sensor can be provided without receptors to provide a control sample in the sensor. In one embodiment, the respective regions comprise different antibodies, enzymes, cell receptors, molecular print assays, nucleic acids (e.g. DNA or RNA). In another embodiment of the invention, different regions of the porous membrane include different functionalities, such as antibodies, enzymes and nucleic acids. Additionally, measurements can be performed to obtain phase changes.

Moreover, particularly when a silicon-based technology is used, it is possible for sensors according to embodiments of the invention to be highly integrated. For example, when the substrate comprises silicon, the light source can be disposed on the sensor chip, as well as electronics including the photodetector. In this embodiment, the photodetector array can include a plurality of pixels, with one pixel associated with a particular region of the porous membrane having a particular receptor. The integrated embodiment can also provide on-chip signal amplification and signal processing electronics, as well as MEMS devices, including MEMS mirrors.

Porous silicon membrane waveguide sensors according to embodiments of the invention are generally low-cost, high sensitivity sensors that are generally capable of detection of wide variety of biological and chemical materials, including simultaneously detecting a plurality of biological or chemical materials. Such sensors are generally cheaper and as described above are generally more sensitive than commercial fiber optic and SPR sensors particularly for low molecular weight species. Applications for sensors according to embodiments of the invention include areas of medicine, environmental monitoring, food safety, and homeland security. Proof-of-principle operation of the sensor has been demonstrated using various chemicals and DNA molecules, as described in the Examples provided below.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Figure 5:
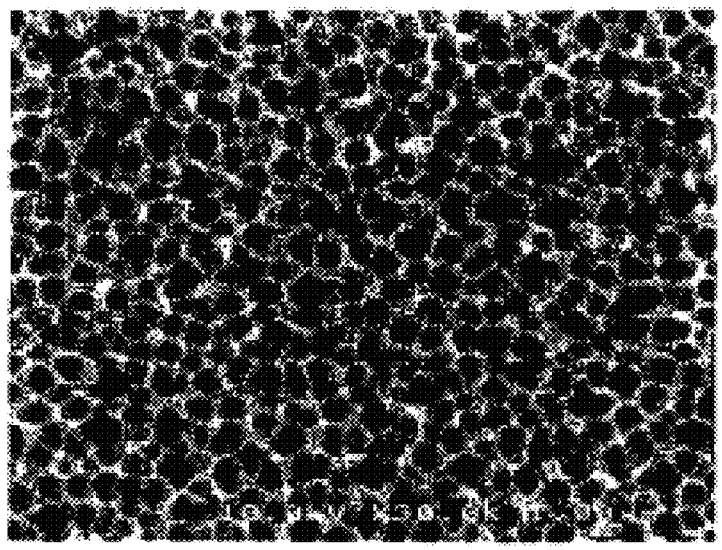
FIG. 5 shows a scanning electron microscopy (SEM) image of a fabricated porous silicon membrane for a sensor in accordance with an embodiment of the invention, evidencing voids.

The fabrication of a sensor in accordance with an embodiment of the invention starts with electrochemical etching of an n-type silicon wafer (<100>, 0.01 Ω·cm) in 5.5% aqueous hydrofluoric acid. A current density of 40 mA/cm$^2$ was applied for 35 seconds. The resulting porous silicon membrane was then removed from the silicon substrate by applying a series of 5 high current pulses (200 mA/cm$^2$ for 4 seconds with 50% duty cycle). This procedure caused electropolishing and subsequent detachment of the porous film from the substrate. During the electropolishing, a slight widening of the pore diameter at the bottom of the porous silicon membrane film occurs. FIG. 5 shows a scanning electron microscopy (SEM) image of the resulting porous silicon membrane, evidencing voids comprising 100 nm diameter pores. In general, 8-10 porous silicon membranes can be fabricated from the same silicon substrate without significantly degrading the quality of the resulting porous silicon membranes.

The porous silicon membrane was then placed on a BK7 glass slide and was oxidized at 500° C. for 5 minutes in an Omegalux LMF-3550 oven, after insertion at 300° C. To build the waveguide structure, 0.25% formvar polymer in ethylene dichloride was dropped onto the surface of a rutile prism (n=2.1252). Ethylene dichloride is then evaporated to leave behind a thin film of formvar polymer (n~1.5, transparent in infrared region). In order to ensure strong adhesion of the porous silicon membrane to the polymer film, the membrane was placed at the thinner edge of the ethylene dichloride solution drop before the solution completely dried. Using this method, no air gap was formed between the polymer film and the porous silicon membrane, or between the polymer film and the prism. The porous silicon membrane was placed such that the larger pore openings were at the air interface to facilitate molecule infiltration. The resulting porous silicon membrane waveguide structure is similar to that described above with respect to FIGS. 1 and 2.

Figure 6:
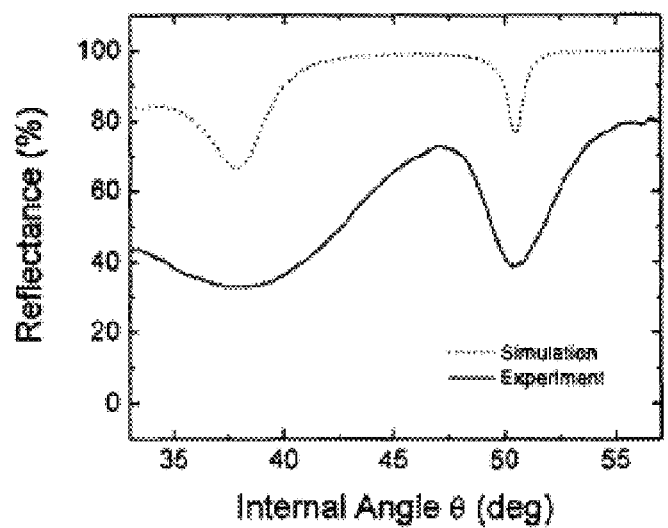
FIG. 6 shows the measurement of the waveguide mode of a fabricated porous silicon membrane for a sensor in accordance with an embodiment of the invention, for simulated and experimental values.

The resulting porous silicon membrane waveguide was characterized by SEM and by optical measurements. Cross-sectional SEM analysis revealed a membrane thickness of 1 micron with a pore density of approximately $5 \times 10^9$ cm$^{-2}$. FIG. 6 shows the measurement of the waveguide mode for simulated and experimental values. Using a Metricon 2010 Prism Coupler, transverse-electric (TE) polarized light from a 1550 nm diode laser was incident on a cubic zirconium prism at variable angle. The reflected light was detected using a germanium photodetector. A waveguide mode is observed at the angle for which the component of the incident light wavevector in the prism parallel to the interface matches that of a waveguide mode. At this angle, light is coupled into the waveguide and not directly reflected back to the photodetector, giving rise to the resonance dip in the measured spectrum shown in FIG. 6. Given the membrane thickness and the polymer refractive index, the membrane refractive index was calculated to be 1.99 and the polymer thickness was determined to be 892 nm by fitting the waveguide mode and substrate mode angles. FIG. 6 shows good agreement between calculated and experimental values. The larger width of the experimental resonance and smaller reflectance amplitude are attributed to scattering losses, which were not taken into account in the calculation. The waveguide mode measured is the 1st order TE mode. Reduction the thickness of the porous membrane or using a higher index prism could be used to measure the 0th order mode.

The sensing operation of the fabricated membrane waveguide is demonstrated by detection of DNA hybridization. In order to enable specific detection of complementary DNA oligonucleotides, the fabricated waveguide was functionalized by first performing a silanization using 4% aminopropyltriethoxysilane. This was followed by the attachment of a monolayer of the crosslinking chemical, Sulfo-SMCC (Pierce), using water and ethanol as the solvent. Before attachment in the porous membrane, 24-base pair thiol modified probe DNA was reduced for 30 minutes by mixing 1:1 by volume DNA in HEPES buffer with TCEP (Pierce) in water and ethanol. In order to screen the negative charges of DNA, which has been reported to cause oxidation and corrosion of convention porous silicon membrane sensors upon hybridization, and to enhance DNA infiltration and surface immobilization, 3 M NaCl was added to the probe DNA solution. Finally, the functionalized porous membrane waveguide sensor was tested through exposure to 24-base pair complementary and non-complementary DNA (all solutions included water, ethanol, and 3M NaCl).

Figure 7:
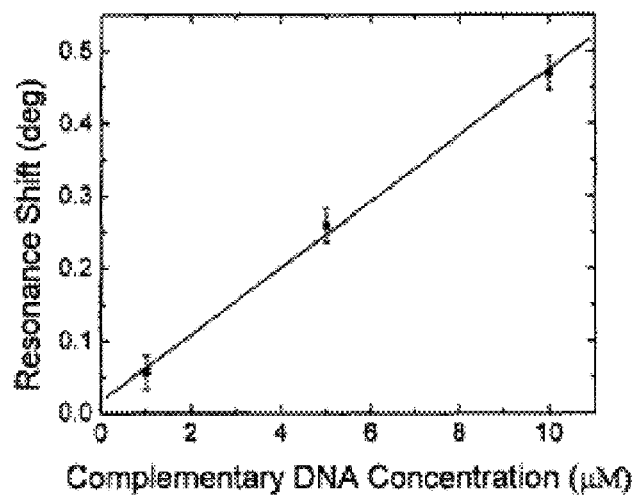
FIG. 7 shows the experimental resonance shifts after the fabricated sensor in accordance with an embodiment of the invention was exposed to different concentrations of complementary DNA.

FIG. 7 shows the experimental resonance shifts after the fabricated sensor was exposed to different concentrations of complementary DNA. When the complementary DNA is exposed to the probe DNA immobilized in the voids, the two DNA strands bind. This hybridization increases the effective refractive index of the porous silicon membrane, which changes the waveguide mode dispersion and hence the waveguide resonance angle measured using the prism coupler. Larger resonance shifts indicate that a greater number of DNA oligonucleotides are hybridized in the porous silicon membrane waveguide. FIG. 7 shows resonance shifts to higher angle for all experiments, suggesting the DNA hybridization-enhanced corrosion problem for conventional p-type porous silicon DNA biosensors is not present sensors fabricated in accordance with the various embodiments of the invention. A linear fit of the experimental data shown in FIG. 7 gives the sensitivity of the sensor, which is found to be 0.048°/uM. Given that the angular resolution of the Metricon prism coupler is 0.002°, the ultimate detection limit of the porous silicon membrane waveguide biosensor is 0.002°/(0.048°/uM)=42 nM. Accordingly, a porous membrane waveguide sensor in accordance with the various embodiments of the invention is capable of nM detection of small molecules, not just the nM detection of proteins observed for conventional SPR sensors.

Additionally, control experiments were performed on the fabricated porous silicon membrane waveguides to demonstrate selectivity. No resonance shift was observed upon exposure to 1 uM non-complementary DNA, suggesting that no binding occurred. Furthermore, no resonance shifts were observed upon exposure to solutions containing only HEPES buffer, TCEP and 3 M NaCl.

Figure 8:
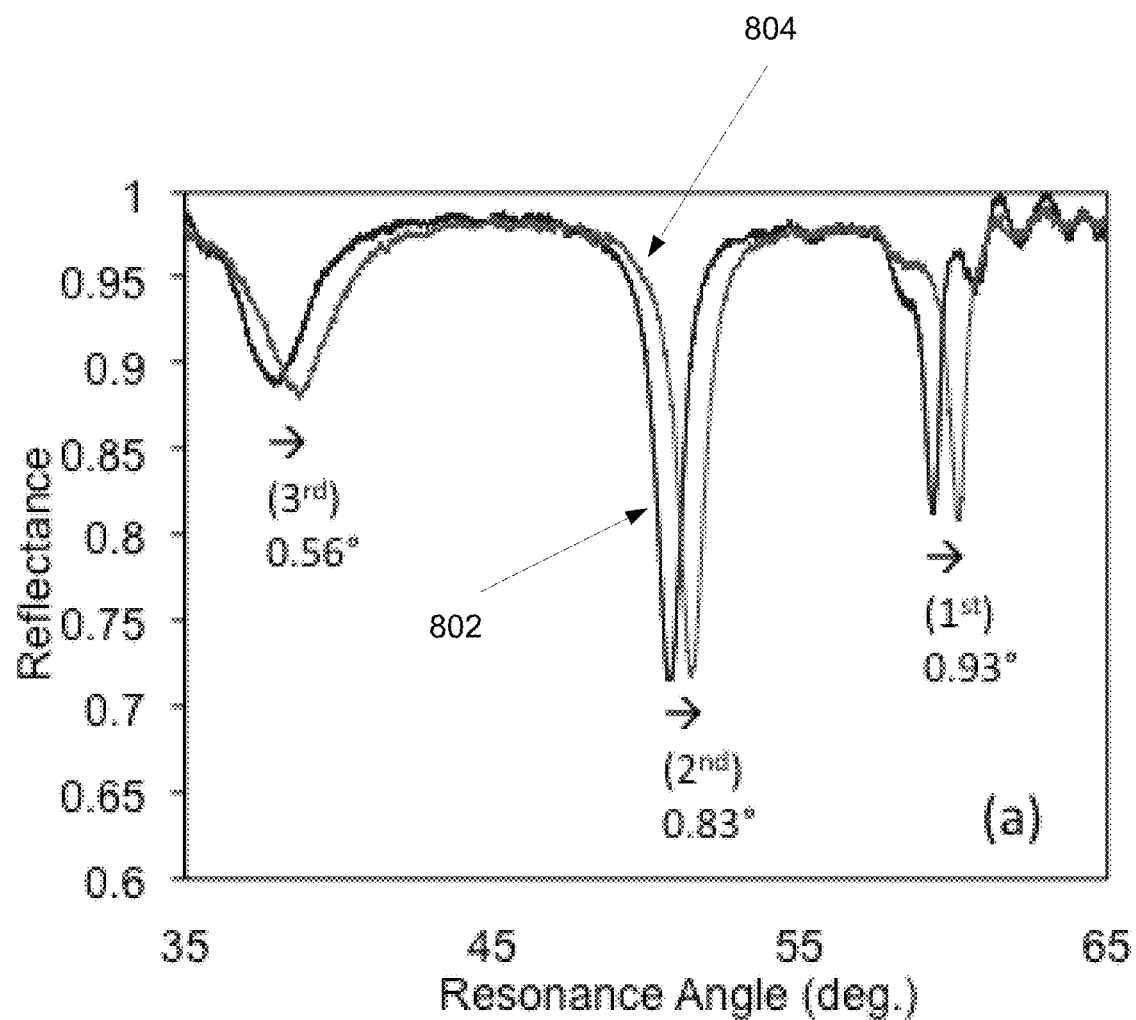
FIG. 8 shows an x-y plot 800 of reflectance as a function of resonance angle for a sensor in accordance with an embodiment of the invention.

FIG. 8 shows an x-y plot 800 of reflectance as a function of resonance angle for a sensor in accordance with an embodiment of the invention. The sensor included a 58% porosity, 1.55 micron thick porous silicon membrane waveguide with polymer cladding before (curve 802) and after (curve 804) attachment of 3-APTES molecules. The reflectance valleys in FIG. 8 corresponds to the angles for which a particular guided mode is supported and will propagate in the waveguide. As shown in FIG. 8, 3 distinct modes are supported ($1^{st}$, $2^{nd}$, and $3^{rd}$). As shown in FIG. 8, the attachment of 3-APTES molecules results in a shift in resonance angles for each mode. The first order mode at the largest resonance angle shows the greatest response (0.93 degree shift) to molecule attachment as compared to the response of the $2^{nd}$ and $3^{rd}$ modes (0.83 and 0.56 degree, respectively), suggesting that this mode is the most sensitive of the three modes.

Optimization of Membrane and Polymer Layer Thicknesses

In order to determine how the detection sensitivity of porous waveguides in accordance with the various embodiments of the invention varies depending on the waveguide design parameters, transfer matrix theory and first order perturbation theory can be employed. Detection sensitivity can be defined as the angular shift of the waveguide resonance divided by the refractive index change of the porous membrane layer due to attachment of small molecules to the void walls. Molecules infiltrated into the voids induce an overall change in the refractive index of the porous dielectric medium. These dielectric function changes, (z), also change the effective index of some waveguide modes, N, in the waveguide. According to perturbation theory, the change of the effective index of a wave due to small molecule attachment can be calculated TE waves by:

$$\Delta(N^2) = \frac{\int_{-\infty}^{\infty} \Delta \varepsilon(z)[E(z)]^2 \, dz}{\int_{-\infty}^{\infty} [E(z)]^2 \, dz} \quad (1)$$

In general, perturbation theory does not generally apply to the infiltration of liquids that fill the entire volume of the porous waveguide. The electric field in each layer of the waveguide structure is found based on transfer matrix theory, and the thickness of the cladding layer is optimized to yield deep and narrow waveguide resonances based on a pole expansion method. With $\Delta \in (z) = 2n \, \Delta n$, $\Delta(N^2) = 2N \, \Delta N$, and $N = n_p \sin \theta$, an analytical expression of the sensitivity of the waveguide for TE modes can be provided as:

$$\begin{aligned} \text{sensitivity} &= \frac{d\theta}{dn} \quad (2) \\ &= \frac{d\theta}{dN} \cdot \frac{dN}{dn} \\ &= \frac{\int_{PSi} [E(z)]^2 \, dz}{\int_{-\infty}^{\infty} [E(z)]^2 \, dz} \cdot \frac{n_{PSi}}{N} \cdot \frac{1}{n_p \cos \theta} \end{aligned}$$

where $n_p$ and $n_{PSi}$ are the refractive index of the prism and the porous membrane, respectively, and $\theta$ is the resonant angle in the prism. The first term on the right hand side of Eq. (2) is the power confinement factor, which is defined as the ratio of the power confined in the porous membrane layer to the total power distributed throughout the entire multilayer waveguide structure. The sensitivity is directly proportional to the power confinement factor and the incident angle in the prism.

Figure 9A:
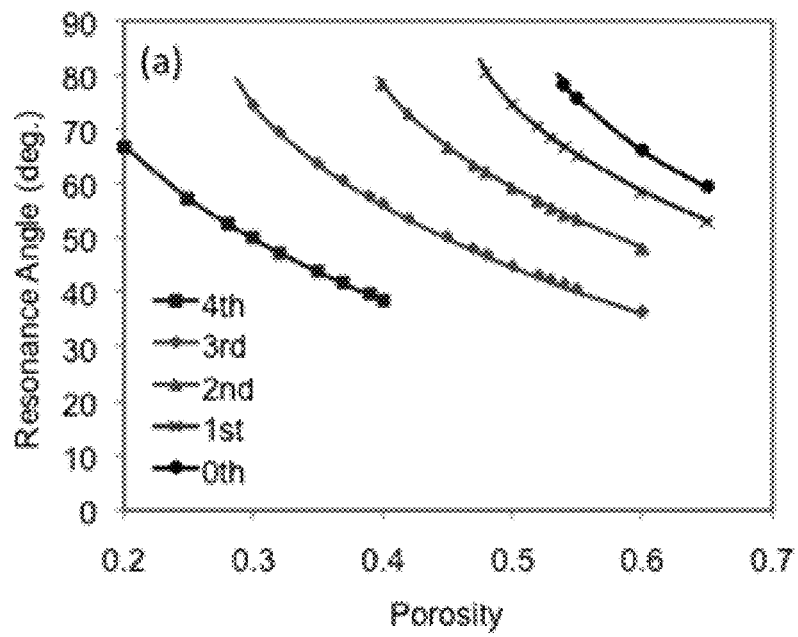
FIGS. 9A and 9B show the theoretically calculated sensitivity and corresponding resonance angles, as a function of the porosity, for a 1.55 m thick polymer-cladded porous silicon membrane waveguide layer in accordance with an embodiment of the invention.
Figure 9B:
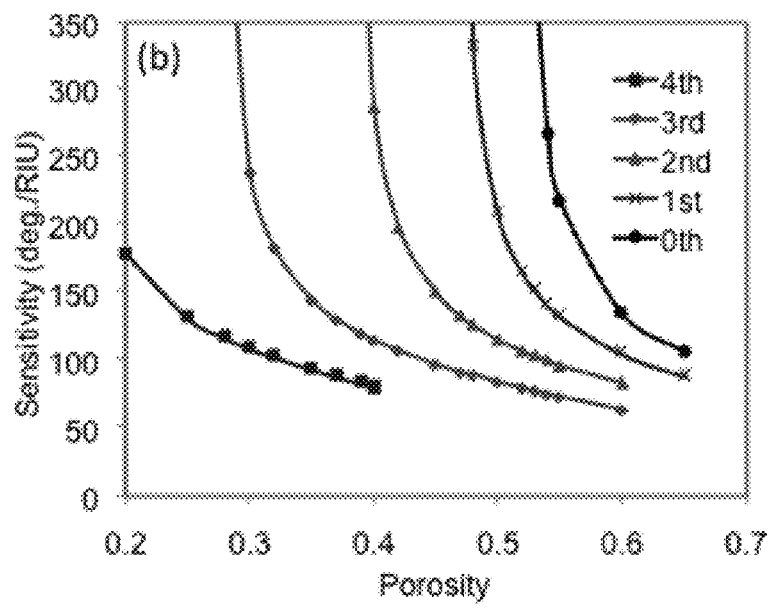

Based on the mathematical methods described above, the theoretically calculated sensitivity as a function of the porosity of a 1.55 m thick polymer-cladded porous silicon membrane waveguide layer was calculated and is plotted in FIG. 9A. The corresponding resonance angles are shown in FIG. 9B. In FIGS. 9A and 9B, each curve corresponds to one waveguide mode. Higher order modes can be supported at lower porosities. For each mode, the sensitivity decreases with increasing porosity of the porous membrane layer until the mode cutoff condition at the critical angle is satisfied. As the incident angle approaches 90 degrees, the sensitivity goes to infinity. At very large incident angles, the 1/cos term dominates the power confinement factor in the sensitivity calculation, while the opposite is true at smaller incident angles. If the thickness of the porous membrane waveguide layer is increased, the curves will be shifted upward and the number of modes supported by the waveguide will also be increased.

Applicants present certain theoretical aspects above that are believed to be accurate that appear to explain observations made regarding embodiments of the invention based primarily on solid-state device theory. However, embodiments of the invention may be practiced without the theoretical aspects presented. Moreover, the theoretical aspects are presented with the understanding that Applicants do not seek to be bound by the theory presented.

Figure 10:
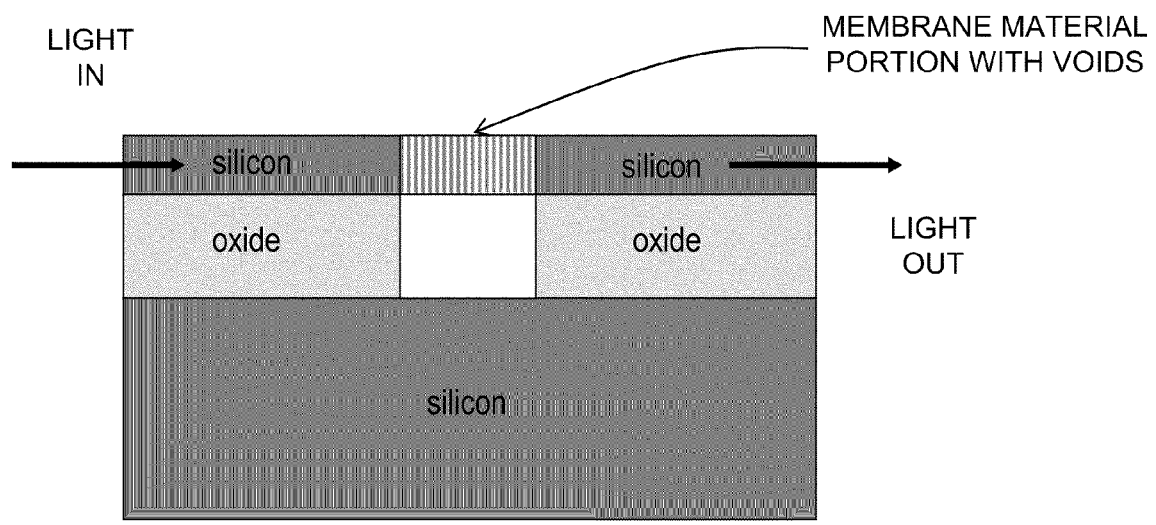
FIG. 10 is a depiction of an alternate exemplary sensor system including a porous membrane waveguide sensor according to an embodiment of the invention for sensing at least one biological target or chemical target.

While various embodiments of the present invention have been described above, it should be understood that they have been presented by way of example only, and not limitation. Numerous changes to the disclosed embodiments can be made in accordance with the disclosure herein without departing from the spirit or scope of the invention. For example, as shown in FIG. 10, a sensor 1000 can be provided in which sensors are formed only in suspended portions of a membrane material. This structure can be formed via the use of silicon-on-insulator (SOI) substrates. In such structures, before or after forming voids in the upper silicon layer to define a sensor region, the portion of the silicon oxide comprising layer beneath the sensor region is removed. Accordingly, air or a liquid buffer is then used as a cladding material on both sides of the membrane. Light can then be coupled into the membrane material as previously described with respect to FIG. 1. Other configurations are also possible. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The Abstract of the Disclosure is provided to comply with 37 C.F.R. §1.72(b), requiring an abstract that will allow the reader to quickly ascertain the nature of the technical disclo-

We claim:

1. A sensor for sensing at least one biological target or chemical target, comprising:
   a membrane consisting of essentially a single layer of porous material that supports generation and propagation of at least one waveguide mode, said single layer of porous material comprising a plurality of voids having an average size<2 microns;
   at least one receptor having structure for binding to said at least one of said biological target or said chemical target within said plurality of voids;
   an optical coupler for coupling light to said membrane sufficient to generate said waveguide mode in said membrane from photons incident on said optical coupler, the optical coupler selected from the group consisting of a prism and a grating; and
   a cladding separating the membrane and the optical coupler, wherein the cladding is selected from the group consisting of an ambient gas layer, a liquid buffer layer, and a layer of polyvinyl formal.

2. The sensor of claim 1, wherein said plurality of voids have an average size<0.5 microns.

3. The sensor of claim 1, wherein said single layer of porous material comprises silicon.

4. The sensor of claim 1, wherein said single layer of porous material comprises at least one of a polymer and a semiconductor.

5. The sensor of claim 1, wherein the cladding is a single layer.

6. The sensor of claim 1, wherein the at least one receptor comprises at least one selected from the group consisting of a chemical receptor, a bioreceptor, an aptamer, a darpin, a polymer, a biopolymer, a molecular imprint polymer, a biomimetic, an antibody or fragment thereof, an enzyme, a cell receptor, a molecular print assay, and a nucleic acid, and combinations thereof.

7. The sensor of claim 1, wherein said membrane supports generation and propagation of one mode in a wavelength range from 1 to 3 microns.

8. The sensor of claim 1, wherein said waveguide mode is at least one of a guided mode and a leaky mode.

9. A sensing system, comprising:
   a sensor for sensing at least one biological target or chemical target comprising a substrate support layer and a membrane supported by the substrate support layer, the substrate support layer having at least one opening to expose the membrane and having a lower index of refraction than the membrane, the membrane consisting essentially of a single layer of porous material that supports generation and propagation of at least one waveguide mode on said support layer, said single layer of porous material comprising a plurality of voids having an average size<2 microns, and at least one receptor having structure for binding to said at least one biological target or chemical target within said plurality of voids;
   an optical block coupler operable for coupling light to said membrane sufficiently to generate said waveguide mode in said membrane from photons propagating in said optical block coupler, the optical block coupler selected from the group consisting of a prism and a grating;
   a cladding layer separating the membrane and the optical block, wherein the cladding is selected from the group consisting of an ambient gas layer, a liquid buffer layer, and a layer of polyvinyl formal;
   a light source for providing said photons; and
   a light detector for detecting said photons that are reflected by said optical block coupler.

10. The system of claim 9, wherein said substrate support layer and said single layer of porous material both comprise silicon.

11. The system of claim 9, wherein the optical path for said photons in said optical block coupler to couple to said membrane is exclusive of said substrate support layer.

12. The system of claim 9, wherein an optical path for said photons in said optical block to couple to said membrane is inclusive of said substrate support layer.

13. The sensor of claim 9, wherein said waveguide mode is at least one of a guided mode and a leaky mode.

* * * * *